United States Patent

Pugliese et al.

Patent Number: 6,114,337
Date of Patent: Sep. 5, 2000

[54] ZWITTERONIC-FATTY ACID COMPOUNDS HAVING ANTI-INFLAMMATORY PROPERTIES

[76] Inventors: Peter T. Pugliese, P.O. Box 307, Bernville Rd., Bernville, Pa. 19506; Peter M. Pugliese, 51 Faust Rd. N., Bethel, Pa. 19507

[21] Appl. No.: 09/200,482

[22] Filed: Nov. 27, 1998

[51] Int. Cl.$^7$ .................................................. A61K 31/495
[52] U.S. Cl. ............................................................ 514/255
[58] Field of Search ............................................ 514/255

[56] References Cited

U.S. PATENT DOCUMENTS

| | | | |
|---|---|---|---|
| 4,544,656 | 10/1985 | O'Sullivan, I | 514/228 |
| 4,753,942 | 6/1988 | O'Sullivan, II | 514/255 |
| 5,091,171 | 2/1992 | Yu et al. | 424/642 |
| 5,248,680 | 9/1993 | Bloomfield | 514/238.8 |
| 5,716,959 | 2/1998 | Theodore et al. | 514/255 |
| 5,736,573 | 4/1998 | Galat | 514/560 |
| 5,854,281 | 12/1998 | Uekama et al. | 514/468 |

*Primary Examiner*—James H. Reamer
*Attorney, Agent, or Firm*—A. R. Eglington

[57] ABSTRACT

A composition and method for treating both superficial and subdermal inflammation is taught by treating an inflamed skin area, muscle, or bone joint, with a therapeutically effective amount of a skin-compatible ester of a zwitterionic aminosulphonic acid (ZASA-Ester) of the formula.

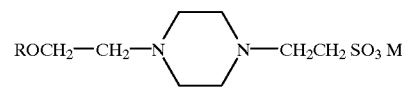

wherein M is an alkali metal, like sodium, and R is a naturally occurring, straight-chain, saturated or unsaturated, aliphatic acid, the esters of which form fatty acids in nature. The most useful of which are the acetic oleic (cis isomer), linoleic, palmitic, and stearic moieties; they occur naturally as glycerides, i.e., esters of glycerol. Also useful are analogs of HEPES like piperazine-N'-(2-ethane sulfonic acid); N-methylpiperazine-N'-(2-ethane sulfonic acid);, and the piperiodine analog of the piperazine ester.

A pharmacologic composition is also provided which comprises at least one amphoteric (Zwitterionic-ester) with a pharmacologically-acceptable topical carrier or base. Other adjunctive pharmaceutical agents may be included to facilitate other than topical administration.

Also useful are analogs of HEPES, like Piperazine-$N^1$(2-ethanesulfonic acid; N-Methylpiperazine-$N^1$(2-ethane-sulfonic acid) and the piperidine analog of the piperazine ester.

9 Claims, No Drawings

ZWITTERONIC-FATTY ACID COMPOUNDS HAVING ANTI-INFLAMMATORY PROPERTIES

CROSS REFERENCE TO OTHER FILINGS

This is a regular patent application submitted for an official filing receipt under 35 U.S. Code Section 111(a). It relates to Disclosure Document No. 425,759, filed October 6, 1997, titled: A New Zwitterionic-Fatty Acid Compound That Is An Anti-Inflammatory and Healing Agent, and a Method to Synthesize the Product From Sodium Salt of HEPES and a Fatty Acid Salt. This disclosure is also a continuation-in-part of my copending provisional application Serial No. 60/066,918, filed Nov. 28, 1997.

FIELD OF THE INVENTION

This inventions relates to pharmacologically-active, anti-inflammatory compounds, and more specifically to long aliphatic chain esters of selected zwitterionic organic compounds derived from naturally occurring taurine. This invention pertains to novel zwitterionic compounds with pharmacologic activity including, but not limited to, their use as an anti-inflammatory agents.

BACKGROUND OF THE INVENTION

Any inflammation that occurs in the mammalian body is the clinical result of a sequence of events known as the arachidonic acid (ARA) cascade. Cell membranes consist of phospholipids, including fatty acids, one of which is ARA. In the inflammation process, the first step is the release of ARA from the phospholipid. The next step is the conversion of ARA into the specific mediator of inflammation. One pathway is the cyclooxygenase enzyme, and the other is called the lipoxygenase pathway. Cortisone, along with other selected steroidal agents, block both inflammation pathways by inhibiting ARA release from the phospholipids.

The mode of action of HEPES-ester is thought to be at the level of leukotrienes B4, but it is also possible that it occurs at higher levels in the inflammatory cascade, perhaps at the phospholipase A2 (PPLA2). Successful Inhibition of PPLA2 action would arrest the aforedescribed cascade effect from being initiated.

Medical science searches for other biochemicals that lack the recognized side effects of prolonged steroid-based (hydrocortisone) medications. One known human biochemical, taurine (2-amino ethanesulfonic acid), synthesis of which occurs in the mammalian liver, has demonstrated anti-inflammatory activity when administered centrally, but not when administered subcutaneously or interperitoneally. N-substituted derivatives of taurine include: 4-(2-Hydroxyethyl)-1-piperazine-ethanesulfonic acid; $C_8H_{18}N_2O_4S$, which derivatives are commonly identified in the technical literature as Hepes (Merck Index, 12th edition monograph #4687). HEPES itself is available commercially from Angus Chemicals, as the sodium salt or, as the free acid. The scientific literature reports that intravenous injection of (14-C) HEPES, or of (3H) taurine, demonstrated rapid clearance, but with a significantly longer half-life compared with taurine. Mahon et al theorized that the greater anti-inflammatory effects of HEPES (sodium salt and the acid), as compared with taurine, may be due to its slower systemic distribution or clearance, in vivo. The prior art suggest that HEPES is a significant agent to reduce cellular inflammation and cellular proliferation. However, the safe delivery systems for the HEPES treatment of inflammation remain to be optimized.

It is thus a principal object of this invention to provide a HEPES-based compound, an ester, and a pharmaceutically acceptable formulation including the ester, that is adapted for use in topically applied products so as to reduce symptoms of skin inflammation, wherein the particular etiology of the inflammation does not call for, or require, the use of antibiotics or germicidal compositions. Improved formulations for epidermal penetration, on bruises, muscle strains and sprains are also areas of useful progressive treatment.

It is another object of the invention to complex the HEPES molecule with selected aliphatic acids, such serving as the active ingredient of topical applications, which permit the HEPES moiety to penetrate the skin and so to better effect its anti-inflammatory nature.

It is a further object of the invention to provide a HEPES-containing active ingredient that is not limited to the known subcutaneous injection or IV infusion routes, but may also effective as a topical formulation.

A still further object of the invention is to provide HEPES esters as a cosmetic formulation ingredient, as a co-emulsifier, usable with topical analgesics.

Still another object of the invention is in a cosmetic preparation to incorporate an anti-skin ageing active ingredient.

These and other objects and benefits of this invention will become apparent from a study of the following specification.

SUMMARY OF THE INVENTION

The present invention relates to a composition and method for the treatment of inflammatory conditions in mammals, by the topical administration of selected Zwitterionic ester compositions, serving as safe and effective substances. Among useful Zwitterionic compounds which are presently preferred; these include EPES, PIPES, BES, POPSO, and most preferably HEPES, when esterified, then alone, or in combination with other therapeutic ingredients. They are employed by applying to an affected area of the skin, a therapeutically effective amount of at least one skin compatible, Zwitterionic-Ester having the generic formula:

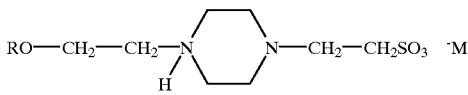

wherein M is an alkali metal and R is a naturally occurring, straight-chain, saturated or unsaturated, aliphatic acid, the esters of which do form fatty acids in nature.

Preferably, a Zwitterionic-ester has at least one pKa value at 20° C. in the range of 6.0–8.3, to permit its use on human skin, i.e., the ester exists mainly in its dipolar form, in the pH range of 6.0–8.3.

The isoelectric (ISO) point is the pH at which the net charge on a molecule in solution is zero. At this pH, amino acids exist almost entirely in the Zwitterionic state, i.e., the positive and negative groups are equally ionized. A solution of amino acids at the ISO point exhibits minimum conductivity, osmotic pressures, and viscosity.

Such dipolar molecules contain, for example, hydroxy groups and amino groups, and also acid groups, like phosphoric, carboxylic, or sulfonics acid groups and, generally have pKa's in the range of 6.15–8.4.

Preferred aliphatic values for the ester moiety of the HEPES ester are n-butanoic; isobutyric, n-valeric, palmitic, and stearic, behenyl, lauric, myristic, (and their isomers), among the saturated aliphatics; and oleic and linoleic, among the unsaturated aliphatics.

The invention also provides a pharmaceutical composition for application to human skin in the treatment of inflammation comprising at least one of the above Zwitteronic-esters as the active ingredient, together with a pharmacologically acceptable topical carrier or base.

These select esters may be useful in the treatment of arthritis, myositis, insect bites, sunburn, psoriasis, atopic dermatitis, and other inflammatory processes of muscle, connective tissue, or skin appendages.

DETAILED DESCRIPTION OF THE INVENTION

The effective proportion of the active ester ingredient, by weight of the formulation, is in the range of 1 to 20%, preferably 5 to 10%. In the most preferred composition, the effective proportion lies in the range of 6 to 8%. Not every compound falling within the general definition given above, is suitable for topical use per the method of the invention. Some few will prove to be contraindicated. Nevertheless, the exclusion of ineffective active ingredients is a matter well within the competence of the skilled pharmacologist in the conduct of the anti-inflammatory evaluation protocols (to be described) for disclosed HEPES-esters.

The topical formulation base is selected from a wide variety of compositions, formulated according to known principals for pharmaceutical purposes. Such compositions include creams, solids, ointments, lotions, and film-forming solutions among others. They may be presented in boxes, jars, or compressible tubes, both collapsible and non-collapsible. The solids may be presented as sticks for rubbing onto the skin. Some of the topical bases may be presented as papers, woven or non-woven fabric pieces, or pads, all being impregnated with composition.

The invention relates to HEPES derivatives which are pharmacologically active as anti-phospholipase and anti-inflammatory compounds specifically, wherein the active ingredients are certain long chain esters of selected zwitterionic compounds, based on an N-substituted taurine, namely aliphatic esters of HEPES.

The novel compounds may exist as at least one of the following five organic groups: ester, ether, urethane, amide, or urea of all of the following known compounds, and their salt forms. Preferred Zwitterionic-esters are prepared from the below listed sulfonic acids.

ACES—N-(2-Acetamido)-2 amino ethane sulfonic acid.
AMPSO—3-[1,1Dimethyl-2 hydroxyethyl amino]-2-hydroxypropane sulfonic acid.
BES—N,N-bis (Hydroxyethyl)-2 aminoethane sulfonic acid.
DIPSO—3-[N,N-bis (hydroxyl ethyl) amino]-2-hydroxypropane sulfonic acid.
CAPS—3-(cyclohexylamino)-1-propane sulfonic acid.
CAPSO—3-(cyclohexylamino)-1-propane sulfonic acid.
CHES—2-(N-cyclohexylamino) ethane sulfonic acid.
HEPPS—N-(2-hydroxy ethyl) piperazine-N'-3-propane sulfonic acid.
HEPES—N-(2-hydroxy ethyl) piperazine-N'-(2-propane sulfonic acid).
HEPPSO—N-(2-hydroxy ethyl) piperazine-N'-2-hydroxypropane sulfonic acid.
MES—2-(N-Morpholino) ethane sulfonic acid.
MOPS—3-(N-Morpholino) propane sulfonic acid.
MOPSO—3-(N-Morpholino)-2 hydroxy propane sulfonic acid.
PIPES—Piperazine-N, N'-bis (2 ethane sulfonic acid).
New Mono PIPES—Piperazine-N'-(2 ethane sulfonic acid).
POPSO—Piperazine-N, N'-bis (2-hydroxy propane sulfonic acid).
TAPS—3-[N-tris-(hydroxy methyl) methyl amine]-2-hydroxy propane sulfonic acid.
TES—N-tris-(hydroxy methyl)-methyl-2-amine ethane sulfonic acid.
EPES—N-ethylpiperazine-N-(2 ethane sulfonic acid).

The precursor compounds listed above are best known in the literature as biological buffers. Many are commonly used as buffering agents in mammalian cell cultures. Manufacturers of these compounds include Angus Chemicals, SIGMA, and British Drug House.

SYNTHESIS OF HEPES ESTERS

Generally, an alkali metal salt of HEPES is catalytically reacted with an alkyl-substituted, either saturated or unsaturated, aliphatic salt, such as methyl oleate, methyl linoleate, methyl palmitate, methyl stearate, methyl myristate, and methyl behenate. They are reacted in equimolecular amounts, carried out either with or without a non-aqueous solvent, such as acetone, and in a temperature range of 0° C. to variable ° C., which is between 0C. and the chosen solvent's reflux temperature. The purification of the crude ester is carried out by means of crystallization in an organic solvent, dissolved in methanol, and recrystallized. As to analytical methodology, preparative high pressure liquid chromatography (HPLC) is followed by TLC, HPLC, and nuclear magnetic resonance (NMR) techniques. Potentiometric titration and bromic titration are done across the double bond to establish identity and purity. The HPLC device is equipped with a variable length, ultraviolet detector.

FIRST PROTOCOL TO EVALUATE CANDIDATE FORMULATIONS FOR SUPPRESSION OF INDUCED SKIN INFLAMMATIONS

Sodium lauryl sulfate solution 0.5% is applied in a patch to four areas on the volar surface forearm. Site one is pretreated with a base formula, site two is pretreated with the base formula plus 10% HEPES ester, while skin sites three and four are left untreated.

After 24 hours, the sites are examined, the erythema and edema on sites one and two are recorded by photographs. Site one is treated with the base product, site three is treated with the base product plus 10% HEPES ester, and sites two and four are untreated controls. Each treated site (two) is treated four times a day. The observed results are recorded as the percent reduction of erythema and edema at the HEPES ester-treated sites over the base formula site and two control treated sites.

GENERAL SYNTHESIS

Active Ingredients for Synthesis Procedure (that have the HEPES-oleate synthesis)

Preparation of HEPES ($C_8H_{18}N_2O_4S$)—Oleate Ester—Compound I

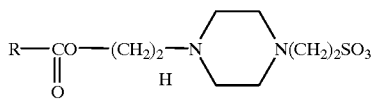

The preparation of Compound I is characterized by catalytically reacting 4-(2-Hydroxyethyl) piperazine-1-ethanesulfonic acid, with salts like methyl oleate, $C_{17}H_{33}CO_2CH_3$, in equimolar amounts. The reaction can be carried out in a non-aqueous solvent. Sodium methoxide is a useful catalyst. The reaction temperature may vary between 0°C. and the solvent reflux temperature. The purification of the compound is carried out by means of crystallization in a solvent such as acetone.

I. THE ESTERS.

Methyl oleate HEPES Na+Na methoxide →HEPES oleate+Methyl alcohol HEPES Na oleate

HEPES ESTERS GENERIC FORMULA

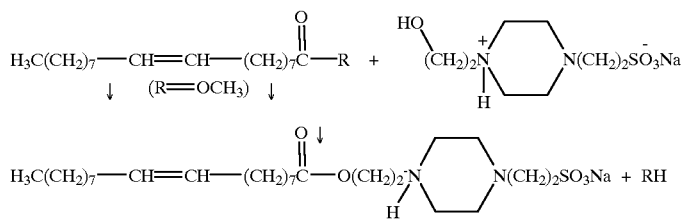

The preparation of Compound I can be carried out by reacting a fatty acid with HEPES (full compound name) or any one of its salt derivatives. One preferred process route is to react HEPES, sodium salt, with methyl oleate and sodium methoxide as a catalyst.

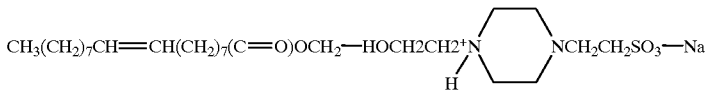

The reactions is carried out with an excess of methyl oleate as a solvent. To ensure the completion of the reaction, removal of side product methanol is carried out.

Preparation of the HEPES oleate: sodium salt 4-(2-Hydroxyethyl) piperazine-1-ethanesulfonic acid, sodium salt, is slowly added to a stirring flask of methyl oleate in equal molar equivalents. The mixture is stirred at room temperature for 15 minutes. Then a catalytic quantity of sodium methoxide is slowly added to the stirring mixture. The reaction mix is stirred for less than five minutes. The reaction mix is then slurried in acetone, then isolated and dried, affording greater than an 80% yield of the title oleate as a white to off-white solid, to wit:

$$CH_3(CH_2)_7CH=CH(CH_2)_7(C=O)OCH_2-HOCH2CH2^+N\diagup\diagdown NCH_2CH_2SO_3-Na$$

WORKING EXAMPLE I

In a 500 ml, 3 neck flask, 114 gms of methyl oleate is added with 100 gms of HEPES, sodium salt (source: Angus Chemical); while stirring, the mixed is warmed to 27–30° C. Once at 27–30° C., 0.4 gms of the sodium methoxide catalyst is added. A mild exotherm is observed, and the contents are slowly heated to 45–50° C. Once at 45–50° C., vacuum is applied to remove methanol to ensure reaction completion.

After two hours at 45–50° C. and under vacuum, the reaction is complete. The vacuum is removed and acetone is added. With the reaction mix in acetone solution it is slowly cooled to 0–5° C. over two hours, and stirred for an additional six hours before isolating the HEPES oleate, sodium salt, in a filter funnel. The white to off-white solid product is then placed in a vacuum oven at 50° C. at 28" of vacuum for six hours to remove any remaining acetone or methanol. A greater than 80% yield is obtained.

WORKING EXAMPLE 2

II. HEPES ether has the structure:

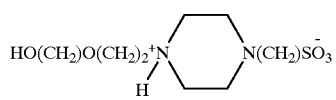

HEPES, Na salt, is reacted with ethylene oxide to form the ether of the below generic structural formula:

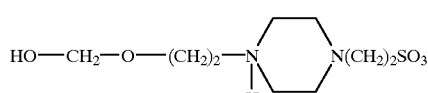

HEPES Ether Compound II

WORKING EXAMPLE 3

III. HEPES urethane has the structure:

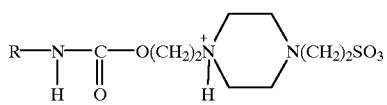

The reaction is carried out by adding isocyanate to the HEPES to form the corresponding urethane below:

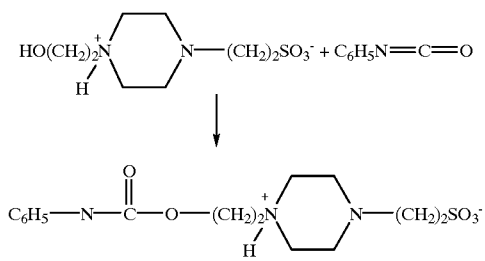

HEPES URETHANE Compound III

WORKING EXAMPLE 4

Certain other analogs and derivatives of HEPES can be synthesized, such as Piperazine-N'-(2-ethane sulfonic acid) I. This can be seen as the mono N-substituted analog of taurine. Another prospective analog is the N-Methylpiperazine-N'-(2 ethane sulfonic acid), II, that is readily prepared. Also, the piperidine analog, III, of the piperazine ester (Comp I) may be usefully synthesized and evaluated,

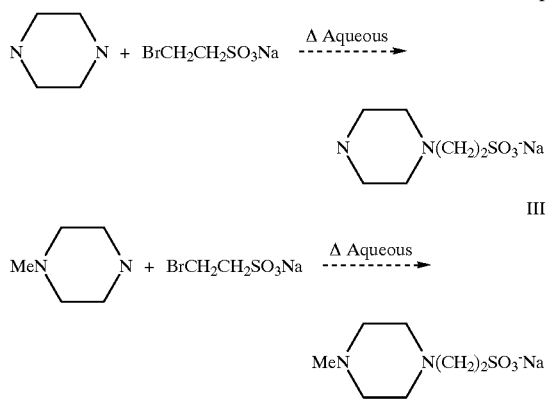

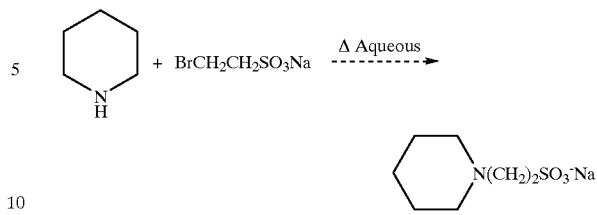

WORKING EXAMPLE 5

PREPARATION OF HEPES-LINOLEATE ESTER-COMP V

The preparation of this ester is conducted by catalytically reacting HEPES, sodium salt, with methyl linoleate, $CH_3(CH_2)_4HC:CH\ CH_2—CH:CH\ (CH_2)_7\ CO_2\ CH_3$, in equimolar amounts. The synthesis follows that of working Example I, yielding the ester V:

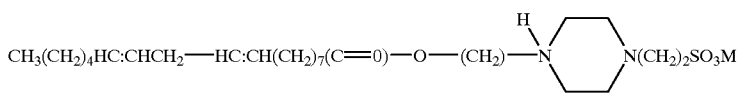

WORKING EXAMPLE 6

PREPARATION OF HEPES-ACETATE ESTER-COMPOUND VI

The preparation of this ester is conducted by catalytically reacting HEPES, sodium salt, with methyl acetate in equimolar amounts, yielding the Compound VI. The product is isolated and purified as described in Working Example I.

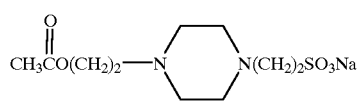

Protocol II for Studies with Dermal Irritation

A new screening method was developed to make rapid assessments on the anti-inflammatory action of the new candidates. The procedure involved the use of a natural irritant, capsaicin*, which candidate is derived from crushed hot peppers (capsicum), and measuring the amount of erythema reduction by the test candidates. Inflammatory reaction are characterzed by pain and tenderness associated with swelling and redness. Most of these clinical signs are attributed to the large influx of blood into the area. Vasoconstricting agents can reduce the amount of swelling and erythema. Hydrocortisone is, in fact, assayed by its ability to blanch the skin, which is a vasoconstrictive effect.

Applying a solution of 0.1% of capsaicin to the forearm of a human volunteer will produce an erythema in less than 20 minutes, usually under five minutes. The degree of erythema is measured with an infra-red detector. An infra-red beam of light at 818 nanometers is directed into the skin over the test sie and the amount of infra-red returned to the surface by reflection indicates the amount absorbed in the skin. An untreated skin area is used as a baseline control, a capsaicin treated area is used as the negative control, and a capsaicin+hydrocortisone (a known vasoconstrictor) serves as the positive control. A positive effect means the erythema induced by the capsaicin is reduced, or is eliminated, as measured by the infra-red detector.

Results

The following reults were obtained with this evaluative protocol. The capsaicin was applied to the skin, and when erythema appeared 10–15 minutes later, the test candidate agent was applied, and the optical reflection measurements were made 30 minutes later.

| Candidate Compound Tested | Millivolts (reflection voltage) |
|---|---|
| Hepes oleate (Compound I) | 3.7 |
| Hepes linoleate (Compound V) | 3.8 |
| Hepes acetate (Compound VI) | 3.0 |
| Hydrocortisone 1% (positive control) | 5.0 |
| Baseline Control (no induced irritation and untreated skin) | 3.5 |
| Capsaicin only (negative control) | 0.5 |

The above data shows that the HEPES counteracted the erythema. Since erythema is a major part of the skin inflammation spectrum, reduction of erythema is a reliable indication of the potential biological anti-inflammatory action of a candidate agent. Indeed, each of the tested esters produced a 70% reduction in erythema compared to one percent hydrocortisone ointment, an established anti-inflammatory steroid.

What is claimed is:

1. A prophylactic anti-inflammatory composition, in dosage unit form, which consists essentially of:
   (a) one or more pharmacologically-acceptable carriers, and
   (b) an amount of a human skin-compatible, organic derivative, being an ester, of a zwitterionic aminosulphonic acid of the formula.

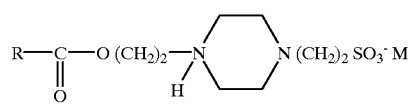

wherein M is an alkali metal and R is a naturally occuring, straight, chain, saturated or unsaturated, aliphatic acid, which amount is effective to counteract dermal inflammation caused by skin irritants upon application to the affected area, as measured by substantially reducing the degree of erythema, indicated by reduced swelling and redness.

2. The composition of claim 1 wherein the organic derivative is the oleic acid ester of 4-(2-hydroethyl)-1-piperazine ethanesulfonic acid, having the molecular formula:

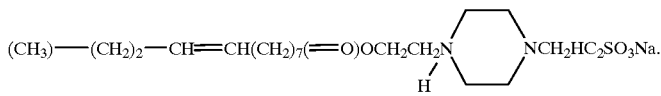

3. The composition of claim 1 wherein the organic derivivative is the linoleic acid ester of 4-(2-hydroxyethyl)-1-piperazine ethanesulfonic acid, having the molecular formula:

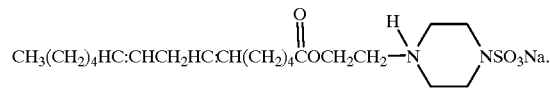

4. The composition of claim 1 wherein the organic derivative is the acetic acid ester of 4-(2-hydroxyethyl)-1-piperazine ethanesulfanic acid having the molecular formula:

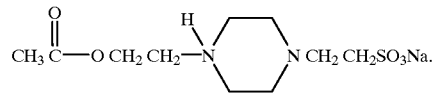

5. A prophylactic anti-inflammatory composition, in dosage unit form, which consists essentially of:
   (a) one or more pharmacologically-acceptable carriers, and,
   (b) an amount of a human skin-compatible, organic derivative, being an ether, of a zwitterionic aminosulphonic acid of the formula.

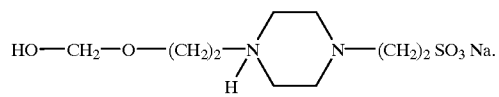

6. A prophylactic anti-inflammatory composition, in dosage unit form, which consists essentially of:
   (a) one or more pharmacologically-acceptable carriers, and
   (b) an amount of a human skin-compatible, organic derivative, being a urethane, of a zwitterionic aminosulphonic acid of the formula

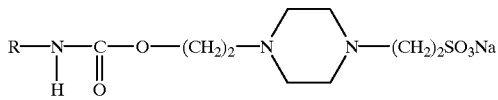

wherein R is an isocyanate ($C_6H_5N$ CO) moiety.

7. In a method of using an anti-inflammatory topical composition containing one or more active ingredients for treating dermal erythema, the improvement characterized by administering a substantially curative amount of a formulated organic derivative, being an ester, of the molecular formula below:

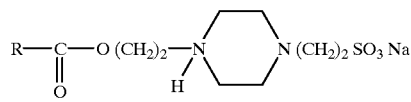

wherein M is an alkali metal and R is a naturally occuring, straight, chain, saturated or unsaturated, aliphatic acid, which amount is effective to counteract dermal inflammation caused by skin irritants upon application to the affected area, as measured by substantially reducing the degree of erythema, indicated by reduced swelling and redness.

8. In a method of using an anti-inflammatory topical composition containing one or more active ingredients for treating dermal erythema, the improvement characterized by administering a substantially curative amount of a formulated organic derivative of (HEPES) of the molecular formula below:

wherein M is an alkali metal and R is a naturally occuring, straight, chain, saturated or unsaturated, aliphatic acid, which amount is effective to counteract dermal inflammation caused by skin irritants upon application to the affected area, as measured by substantially reducing the degree of erythema, indicated by reduced swelling and redness.

9. In a method of using an anti-inflammatory topical composition containing one or more active ingredients for treating dermal erythema, the improvement characterized by administering a substantially curative amount of an organic derivative of (HEPES) of the molecular formula below:

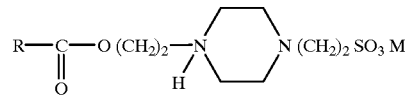

wherein M is an alkali metal and R is a naturally occuring, straight, chain, saturated or unsaturated, aliphatic acid, which amount is effective to counteract dermal inflammation caused by skin irritants upon application to the affected area, as measured by substantially reducing the degree of erythema, indicated by reduced swelling and redness.

* * * * *

UNITED STATES PATENT AND TRADEMARK OFFICE
CERTIFICATE OF CORRECTION

PATENT NO.    : 6,114,337
DATED         : September 5, 2000
INVENTOR(S)   : Pugliese et al.

Page 1 of 1

It is certified that error appears in the above-identified patent and that said Letters Patent is hereby corrected as shown below:

Claims,
In the claims, as to dependent claims 2 and 3 only, the structural formulas should be corrected to read:

Column 10, line 13, claim No. 2:
2.    The composition of claim 1 wherein the organic derivative is the oleic acid ester of 4- (2-hydroethyl)-1-piperazine ethanesulfonic acid, having the molecular formula:

Column 10, line 23, claim No. 3:
3.    The composition of claim 1 wherein the organic derivative is the linoleic acid ester of 4-(2-hydroxyethyl)-1-piperazine ethanesulfonic acid, having the molecular formula:

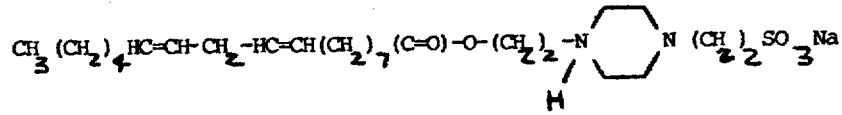

Signed and Sealed this

Fifth Day of February, 2002

Attest:

JAMES E. ROGAN
Attesting Officer     Director of the United States Patent and Trademark Office